United States Patent [19]

Vlock

[11] Patent Number: 4,937,066

[45] Date of Patent: Jun. 26, 1990

[54] ZINC CONTAINING ORAL COMPOSITIONS

[75] Inventor: Richard S. Vlock, Gloversville, N.Y.

[73] Assignees: David G. Vlock; Lawrence Rosen, both of New York, N.Y.

[21] Appl. No.: 369,787

[22] Filed: Jun. 22, 1989

[51] Int. Cl.$^5$ .......................... A61K 7/16; A61K 7/18; A61K 7/20; A61K 7/24

[52] U.S. Cl. ......................................... 424/52; 424/49; 424/53; 424/55; 424/613; 424/614; 424/641; 424/643; 424/673

[58] Field of Search ....................... 424/49, 52, 53, 55, 424/613, 614, 641, 643, 673

[56] References Cited

U.S. PATENT DOCUMENTS

| | | | |
|---|---|---|---|
| 4,022,880 | 5/1977 | Vinson et al. | 424/55 |
| 4,100,269 | 7/1978 | Pader | 424/55 |
| 4,138,477 | 2/1979 | Gaffar | 424/52 |
| 4,144,323 | 3/1979 | Lamberti | 424/49 |
| 4,289,754 | 9/1981 | Dhabhar et al. | 424/55 |
| 4,289,755 | 9/1981 | Dhabhar et al. | 424/55 |
| 4,325,939 | 4/1982 | Shah | 424/55 |
| 4,425,325 | 1/1984 | Ritchey et al. | 424/49 |
| 4,689,214 | 8/1987 | Niles et al. | 424/49 |
| 4,749,561 | 6/1988 | Lane et al. | 424/49 |
| 4,749,562 | 6/1988 | Lane et al. | 424/49 |

*Primary Examiner*—Shep K. Rose
*Attorney, Agent, or Firm*—Lawrence Rosen

[57] ABSTRACT

An ammonium or alkali metal zinc tartrate used in oral compositions such as mouthwashes, gingival and subgingival irrigating solutions, dentifrices, and the like as well as in other preparations for treating oral lesions.

11 Claims, No Drawings

ZINC CONTAINING ORAL COMPOSITIONS

The present invention relates to oral compositions containing a zinc metal complex, and more particularly, to oral compositions containing minor amounts of an ammonium or alkali metal zinc tartrate.

BACKGROUND OF THE INVENTION

It has been recognized for some time that zinc ions derived from zinc compounds employed in dentifrices, oral rinses, mouthwashes and the like have the beneficial effect of reduction of calculus formation and undesirable mouth odor. Zinc chloride has been used for many years, but it is very astringent and has an unpleasant taste that is difficult to mask. In a mouthwash or oral rinse formulation zinc chloride has a pH of about 3.0 which accounts for its high level of astringency.

Insoluble zinc salts such as zinc citrate and zinc carbonate have been used in dentifrice compositions (Pasternak U.S. Pat. No. 1,861,189 and Bley U.S. Pat. No. 1,943,467). Moreover, zinc citrate has been used for periodontal treatment and in dentifrices as a calculus and plaque control agent. Pader in U.S. Pat. No. 4,100,269 has claimed a long list of insoluble zinc compounds all of which do not provide a sufficient amount of zinc ions because of poor solubility.

In U.S. Pat. No. 4,289,755 (Dhabhar) insoluble zinc citrate is employed and solvated by means of an excess of citric acid in an attempt to overcome the relative insolubility problem of zinc compounds. U.S. Pat. No. 4,289,754, also issued to Dhabhar, employs sodium or ammonium zinc citrate as a novel soluble zinc compound, partially overcoming the problem of solubility discussed in U.S. Pat. No. 4,289,755. However, the solubility of sodium zinc citrate is given as only 1.17 g/100 ml, thus precluding a concentration of the zinc salt of more than about 1.2%. In U.S. Pat. No. 4,469,674, zinc salicylate is employed as a source of zinc ions. As set forth above, due to insolubility of the zinc citrate it is impossible to formulate high concentrations of zinc ions. The sodium zinc citrate of U.S. Pat. No. 4,325,939 is stated to have a solubility of about 1.2%, which, while greater than that of zinc citrate, still falls short of providing a desirable concentration of zinc ions.

BRIEF DESCRIPTION OF THE INVENTION

In accordance with the invention novel zinc derivatives, alkali metal or ammonium zinc tartrates, have been prepared which are stable, freely soluble in water, have an almost neutral pH and a lower astringency than other zinc compounds. The ammonium or alkali metal zinc tartrates are stable at pH 7.5 or higher and are not precipitated or deactivated by fluoride ions, which is another problem recognized in the prior art. Moreover, these complexes are soluble to the extent of about 31 grams per 100 ml of water at pH 7.5 and thus can be prepared in aqueous solutions of up to 30% by weight, if desired.

DETAILED DESCRIPTION OF THE INVENTION

An alkali metal or ammonium zinc tartrate $M_2ZnC_4H_4O_6$, wherein M is ammonium or an alkali metal, preferably sodium or potassium, is prepared by admixing a suspension of zinc tartrate in water with ammonium hydroxide or alkali metal hydroxide until the solution is clear and all of the zinc tartrate is dissolved. The solution is then adjusted to pH 7.5 by the addition of an aqueous solution of tartaric acid. The resulting solution can be used as is or evaporated to dryness to obtain the solid complex. The reaction may be carried at ambient temperature in water, as set forth in the following example.

EXAMPLE

In a suitable reaction vessel, 3 grams of zinc tartrate was suspended in 20 cc of water, and the suspension was stirred mechanically. Ammonium hydroxide solution was added dropwise until all the zinc tartrate was dissolved. A concentrated solution of tartaric acid was added dropwise until the solution, which had an alkaline pH, was brought down to a pH of 7.5. The clear solution was evaporated under gentle heat in a suitable vessel to obtain the solid zinc complex. The powdered material was odorless and very soluble in water that had been adjusted to pH 7.5 by addition of ammonium hydroxide.

When the powdered material was admixed with a sodium or potassium hydroxide aqueous solution and heated, ammonia gas was liberated. When a small amount of the powdered product was heated in a bunsen burner flame on a piece of platinum foil it melted, then carbonized, and finally decomposed to a white residue of zinc oxide.

In a similar manner, other alkali metal zinc tartrate complexes are produced, using sodium or potassium hydroxide in place of the ammonium hydroxide. For example, potassium zinc tartrate is produced when potassium hydroxide is employed.

The invention is further illustrated by the following formulations:

| FORMULATION A - A Mouthwash and Oxygenating Rinse | |
|---|---|
| Water | 400 ml |
| Urea Peroxide | 40 gm |
| Ammonium Zinc Tartrate | 10 gm |
| Sodium Lauryl Sulfate | 1.0 gm |
| Sodium Saccharin | 0.125 gm |
| Alcohol | 10 ml |
| Flavor | 5 ml |
| Color | q.s. |

| FORMULATION B - A Toothpaste | |
|---|---|
| Component | Parts by Weight |
| Glycerin | 10.00 |
| Sorbitol 70% in water | 10.00 |
| Dicalcium Phosphate | 30.00 |
| Sodium Lauryl Sulfate | 1.50 |
| Ammonium Zinc Tartrate | 5.00 |
| Sodium Fluoride | 2.00 |
| Sodium Carboxymethyl Cellulose | 2.00 |
| Magnesium Aluminum Silicate | 0.80 |
| Methyl Paraben[1] Preservative | 0.06 |
| Propyl Paraben[2] Preservative | 0.02 |
| Flavor | 1.00 |
| Distilled Water | Balance to 100.00 |

[1]Methyl-p-hydroxybenzoate
[2]Propyl-p-hydroxybenzoate

| FORMULATION C - An Antiplaque Dentifrice | |
|---|---|
| Component | Parts by Weight |
| Glycerin | 15.00 |

FORMULATION C - An Antiplaque Dentifrice

| Component | Parts by Weight |
| --- | --- |
| Sorbitol 70% in water | 5.00 |
| Dicalcium Phosphate | 30.00 |
| Sodium Monofluorophosphate | 2.00 |
| Sodium Lauryl Sulfate | 2.00 |
| Sodium Carboxymethyl Cellulose | 2.00 |
| Ammonium Zinc Tartrate | 2.00 |
| Sodium Zinc Tartrate | 1.00 |
| Triclosan[3] Bacteriostat | 0.20 |
| Flavor | 1.00 |
| Distilled Water | Balance to 100.00 |

[3]5-Chloro-2-(2,4-dichlorophenoxy) phenol

In the prior art formulations containing both zinc ions and fluoride ions were not practical; since, as discussed above, insoluble zinc fluoride was formed, thereby effectively eliminating both ions from the solution. In contrast, the novel ammonium or alkali metal zinc tartrates of the present invention are compatible with fluoride ions over a wide range of concentrations without forming any insoluble precipitates. Thus, incorporating the protective action of fluoride and the antiplaque action of zinc in a single oral rinse or dentifrice formulation is entirely practical. For example, the preferred liquid dentifrices may be conveniently prepared by simple addition of ingredients, in no particular order, to a water or water/alcohol solvent system containing the aforementioned zinc complex and fluoride compound.

Optional ingredients being, for example, a humectant such as glycerine, sorbitol, polyethylene glycol, and the like to give a moist feel in the mouth, generally in amounts up to about 20.0 percent by weight, and preferably from about 5.0 to about 20.0 percent by weight. Additional additives include, but are not limited to, a nonionic antimicrobial agent such as Triclosan, generally from about 0.1 percent to 2.0 percent, preferably from about 0.2 percent to 0.5 percent; a natural or synthetic sweetening agent such as dextrose, levulose, mannitol, saccharin, cyclamate, and the like, generally from about 0.05 to about 2.0 percent by weight; a flavoring agent such as peppermint oil, spearmint oil, wintergreen oil (methyl salicylate), clove oil, anise oil, orange oil and the like, generally from about 0.01 to about 2.0 percent by weight; and a surface-active or sudsing agent such as, for example, a sodium alkyl benzene sulfonate, sodium alkyl sulfate or a nonionic or anionic organic synthetic detergent, generally from about 0.05 to about 10.0 percent by weight preferably from about 0.5 to about 5.0 percent by weight. All the foregoing are conventional surfactants utilized in dentifrice formulations. As set forth in U.S. Pat. No. 4,469,764 (Shah) in substantially solid or semi-solid oral compositions such as dental creams, pastes and gels, the liquids and solids should be proportioned to form an extrudable creamy mass of desirable consistency. Liquids in these formulations will generally comprise chiefly water, glycerin, sorbitol, propylene glycol or the like, including suitable mixtures thereof.

It is usually advantageous to employ a mixture of both water and a humectant or binder such as glycerin or sorbitol, preferably glycerin. The total liquid content will generally be about 20 to 75 percent by weight of the formulation. It is also preferred to use a gelling agent such as a natural or synthetic gum and gumlike material, e.g. Irish moss, gum traganth, xanthan gum, Veegum regular, sodium carboxymethylcellulose, polyvinylpyrrolidone, starch and the like. The Irish moss and sodium carboxymethylcellulose are particularly compatible and are preferred gelling agents. The gum content is usually in an amount up to about 10 percent and preferably about 0.5 to 5 percent by weight of the formulation.

An essential ingredient in dental cream formulations is an effective abrasive amount of a suitable dental abrasive, generally from about 10 to about 60 percent by weight and preferably from about 20 to about 50 percent by weight. As noted previously, this abrasive must not interact with either the zinc or fluoride component. Typical compatible abrasives include, for example, insoluble metaphosphates, finely divided silicas, bentonite and the like. The preferred abrasive is silica.

Various other materials may be incorporated as adjuvants in dental creams. Examples thereof are coloring or whitening agents, preservatives, silicones, chlorophyll compounds, ammoniated materials such as urea, diammoniumphosphate and mixtures thereof, and other constituents. A small amount of colloidal silica, for example, is often incorporated into toothpaste formulations as a thickener, giving some body to the formulation upon swelling when in contact with water. The foregoing adjuvants are suitably selected and incorporated in the instant compositions in amounts which do not have a substantially adverse affect on the properties and characteristics desired for the particular type of composition.

It will be further understood that the invention as described and illustrated above can be modified without departing from the basic concept, that is the use in oral compositions of ammonium or alkali metal zinc tartrate as a source of zinc ions either in the presence or absence of fluoride ions.

What is claimed is:

1. An oral composition comprising about 0.01 to 1% by weight of an anticaries and/or antiplaque- effective fluoride compound, about 0.1 to 15.0% by weight of an ammonium or alkali metal zinc tartrate complex, and a carrier suitable for use in an oral cavity.

2. The oral composition of claim 1 wherein the fluoride compound is selected from the group consisting of sodium fluoride, potassium fluoride, stannous fluoride, and sodiummonofluorophosphate.

3. The oral composition of claim 1 containing a nonionic antimicrobial agent.

4. The oral composition of claim 1 wherein said zinc complex is ammonium zinc tartrate.

5. The oral composition of claim 1 wherein the zinc complex is in the form of sodium zinc tartrate.

6. The oral composition of claim 1 wherein the zinc complex is present in an amount from about 0.2% to about 10%.

7. The oral composition of claim 1 being a toothpaste.

8. A mouthwash composition comprising about 0.01 to 1% by weight of an anticaries-effective fluoride compound, about 0.1 to 15% by weight of an ammonium or alkali metal zinc complex, about 2 to 40% by weight ethyl alcohol, about 0 to 20% by weight humectant, about 0 to 12% by weight surface active agent, about 0 to 0.5% sweetening agent, about 0 to 0.3% by weight flavoring agent, about 0 to 15% by weight urea peroxide, about 0.1 to 5.0% an antimicrobial, and the balance water.

9. The mouthwash of claim 8 wherein said zinc complex is ammonium zinc tartrate.

10. The mouthwash of claim 8 wherein said zinc complex is sodium zinc tartrate.

11. The mouthwash of claim 8 wherein said zinc complex is potassium zinc tartrate.

* * * * *